(12) United States Patent
Burgaud et al.

(10) Patent No.: US 7,282,067 B2
(45) Date of Patent: Oct. 16, 2007

(54) COMPOSITION FOR DYEING KERATIN FIBRES, CONTAINING AN ALCOHOL OXIDASE, AND PROCESS USING THIS COMPOSITION

(75) Inventors: Herve Burgaud, Damartin En Goele (FR); Rui Pereira, Montevrain (FR)

(73) Assignee: L'Oreal, Paris (FR)

( * ) Notice: Subject to any disclaimer, the term of this patent is extended or adjusted under 35 U.S.C. 154(b) by 44 days.

(21) Appl. No.: 10/320,709

(22) Filed: Dec. 17, 2002

(65) Prior Publication Data

US 2003/0154563 A1    Aug. 21, 2003

(30) Foreign Application Priority Data

Dec. 17, 2001  (FR) .................................. 01 16317

(51) Int. Cl.
*A61K 7/13* (2006.01)
(52) U.S. Cl. ...................... 8/405; 8/401; 8/406; 8/410; 8/411; 8/412; 8/421; 8/424
(58) Field of Classification Search ............... 8/405, 8/401, 406, 410, 421, 411, 412, 424
See application file for complete search history.

(56) References Cited

U.S. PATENT DOCUMENTS

| 5,538,517 A | 7/1996 | Samain et al. ............. 8/423 |
| 5,849,041 A | 12/1998 | Kunz et al. ............... 8/408 |
| 6,312,479 B1 * | 11/2001 | Maubru ................... 8/408 |

FOREIGN PATENT DOCUMENTS

| DE | 23 59 399 | 6/1975 |
| DE | 38 43 892 A1 | 6/1990 |
| DE | 41 33 957 A1 | 4/1993 |
| DE | 195 43 988 A1 | 5/1997 |
| DE | 100 16 279 A1 | 10/2001 |
| DE | 100 57 532 A1 | 5/2002 |
| DE | 100 57 545 A1 | 5/2002 |
| EP | 0 310 675 | 4/1989 |
| EP | 0 770 375 A1 | 5/1997 |
| FR | 2 733 749 | 11/1996 |
| FR | 2 750 048 | 12/1997 |
| FR | 2 769 219 | 4/1999 |
| GB | 1026978 | 3/1963 |
| GB | 1153196 | 6/1966 |
| JP | 63-169571 | 7/1988 |
| JP | 5-163124 | 6/1993 |
| WO | WO94/08969 | 4/1994 |
| WO | WO94/08970 | 4/1994 |
| WO | WO96/15765 | 5/1996 |
| WO | WO 00/78273 | * 12/2000 |
| WO | WO 02/ 47633 | 6/2002 |

OTHER PUBLICATIONS

English abstract of JP Patent No. 02000344638 A, Dec. 12, 2002.*
English abstract of JP Patent No. 02001172142 A, Jun. 26, 2001.*
English abstract of JP Patent No. 02001240520 A, Sep. 4, 2001.*

* cited by examiner

*Primary Examiner*—Eisa Elhilo
(74) *Attorney, Agent, or Firm*—Nixon & Vanderhye P.C.

(57) ABSTRACT

The present invention relates to a composition for dyeing keratin fibres, and in particular human keratin fibres such as the hair, containing, in a support that is suitable for dyeing, at least one oxidation dye precursor, characterized in that it comprises at least one alcohol oxidase enzyme and at least one substrate for the said enzyme. This patent application also relates to a process for dyeing keratin fibres, which consists in applying this composition, and also to a dyeing "kit".

29 Claims, No Drawings

COMPOSITION FOR DYEING KERATIN FIBRES, CONTAINING AN ALCOHOL OXIDASE, AND PROCESS USING THIS COMPOSITION

The present invention relates to a composition for dyeing keratin fibres, containing at least one oxidation dye precursor, such that it also comprises at least one alcohol oxidase enzyme and at least one substrate for the said enzyme.

It is known practice to dye keratin fibres, and in particular human hair, with dye compositions containing oxidation dye precursors, in particular ortho- or para-phenylenediamines, ortho- or para-aminophenols, and heterocyclic compounds, which are generally referred to as oxidation bases. These oxidation bases, are colourless or weakly coloured compounds which, when combined with oxidizing products, may give rise to coloured compounds by a process of oxidative condensation.

It is also known that the shades obtained with these oxidation bases may be varied by combining them with couplers or coloration modifiers, the latter being chosen especially from aromatic meta-diamines, meta-aminophenols, meta-diphenols and certain heterocyclic compounds such as indole compounds.

The variety of molecules used as oxidation bases and couplers makes it possible to obtain a wide range of colours.

The "permanent" coloration obtained by means of these oxidation dyes must moreover satisfy a certain number of requirements. Thus, it must have no toxicological drawbacks and it must allow shades of the desired intensity to be obtained and have good resistance to external agents (light, bad weather, washing, permanent waving, perspiration and rubbing).

The dyes must also allow white hairs to be covered and, lastly, they must be as unselective as possible, that is to say that they must allow the smallest possible differences in coloration to be produced over the entire length of the same keratin fibre, which is generally differently sensitized (i.e. damaged) between its end and its root.

The dyeing is generally performed in strongly alkaline medium, in the presence of hydrogen peroxide. However, the use of alkaline media in the presence of hydrogen peroxide has the drawback of causing considerable degradation of the fibres, and also bleaching of keratin fibres, which is not always desirable.

The oxidation dyeing of keratin fibres may also be performed using oxidizing systems other than hydrogen peroxide, such as enzymatic systems. Thus, patent application FR 2 769 219 describes the use of a uricase enzyme and of its uric acid substrate in oxidation dyeing to dye keratin fibres. Patent application EP-A-0 310 675 describes the use of oxidation dye precursors of benzenic type in combination with enzymes such as pyranose oxidase and glucose oxidase. The problem of the lack of solubility of the donor, which is especially the case for uric acid which is the donor for uricase, also occasionally arises.

The aim of the present invention is to provide novel compositions for dyeing keratin fibres by oxidation dyeing, which respect the nature of the keratin fibre and which do not have the solubilization and crystallization problems encountered especially with the uric acid/uricase system.

The Applicant has now discovered, advantageously and unexpectedly, that it is possible to achieve this aim by using at least one enzyme of alcohol oxidase type and a substrate for the said enzyme in a composition for dyeing keratin fibres, and in particular human keratin fibres such as the hair.

The composition according to the invention contains, in a support which is suitable for dyeing, at least one oxidation dye precursor, this composition being such that it comprises at least one alcohol oxidase enzyme and at least one substrate for the said enzyme.

The composition according to the invention is a composition for dyeing keratin fibres, and in particular human keratin fibres such as the hair, containing, in a support that is suitable for dyeing, at least one oxidation dye precursor, characterized in that it comprises at least one alcohol oxidase enzyme as sole enzyme for the composition, chosen from primary alcohol oxidases (EC1.1.3.13), secondary alcohol oxidases (EC 1.1.3.18), long-hydrocarbon-chain alcohol oxidases (EC 1.1.3.20), polyvinyl alcohol oxidases (EC 1.1.3.30), vanillyl alcohol oxidase (EC 1.1.3.38) and aromatic alcohol oxidases (EC 1.1.3.7), and at least one substrate for the said enzyme.

The compositions according to the present invention produce dyeing results with strong, unselective and fast colours, and these compositions are capable of generating novel powerful dyes that can give varied shades of intense and uniform colour, without any significant degradation of the hair. In addition, it has been noted that the use of such a composition improves the hold of permanent-waved hair and reduces the porosity of the hair.

In the context of the present invention, the alcohol oxidase enzymes that may be used in the dye composition in accordance with the invention belong to the class E.C.1.1.3 of the enzyme nomenclature (see Enzyme Nomenclature, Academic Press Inc; 1992).

The said enzymes may be chosen especially from primary alcohol oxidases (EC1.1.3.13), secondary alcohol oxidases (EC 1.1.3.18), long-hydrocarbon-chain alcohol oxidases (EC 1.1.3.20), polyvinyl alcohol oxidases (EC 1.1.3.30), vanillyl alcohol oxidase (EC 1.1.3.38) and aromatic alcohol oxidases (EC 1.1.3.7), also known as aryl alcohol oxidases.

Alcohol oxidase enzymes form a particular class of 2-electron oxidoreductase enzymes.

The alcohol oxidase enzyme used in the dye composition according to the invention may be derived from an extract of plants, of animals, of micro-organisms (bacterium, fungus, yeast, microalga or virus), of differentiated or undifferentiated cells, obtained in vivo or in vitro, unmodified or genetically modified, or synthetic (obtained by chemical or biotechnological synthesis).

Examples that may be mentioned in particular are the genera Pinus, *Gastropode, Manduca, Pichia, Candida*, Pleurotus and Pseudomonas, and even more particularly the following species: *Pinus strobus*, which is a species of plant origin, *Gastropode mollusc* and *Manduca sexta*, which are of animal origin, *Pichia pastoris* and *Candida boidinii*, which are yeasts, *Pleurotus pulmonarius*, which is a fungus, and *Pseudomonas pseudoalcaligenes*, which is a bacterium.

Generally, the concentration of alcohol oxidase enzyme used in the dye composition is between 0.005% and 40% by weight relative to the total weight of the said composition, and preferably between 0.05% and 10% by weight relative to the weight of this composition.

The enzymatic activity of the alcohol oxidase enzymes used in accordance with the invention may be defined from the oxidation of the donor under aerobic conditions. One unit U corresponds to the amount of enzyme leading to the generation of 1 µmol of hydrogen peroxide per minute at a given pH and at a temperature of 25° C.

The amount of alcohol oxidase is preferably between 0.2 U and $4 \times 10^8$ U units per 100 g of dye composition.

The substrate(s) for the said enzyme, also known as donors for the enzyme, used in the compositions according to the invention are chosen from alcohols and oxidation dye precursors bearing at least one alcohol function.

In practical terms, the substrate for the enzyme is, generally, commonly contained in the prior-art compositions for the oxidation dyeing of keratin fibres either as an oxidation dye precursor or as a solvent or preserving agent when it is an alcohol.

The use of the composition in accordance with the invention can reduce the risks associated with the handling of hydrogen peroxide. Furthermore, the concentration of preserving agents in the compositions according to the present invention may be reduced by supplying compounds containing an alcohol function which also have preserving properties.

According to a first preferred variant, the substrate for the enzyme is an alcohol. The nature of this substrate varies as a function of the nature of the alcohol oxidase enzyme used.

This substrate for the enzyme will preferably be an alcohol chosen from primary alcohols, secondary alcohols, long-hydrocarbon-chain alcohols and aromatic alcohols. For example, donors for the primary alcohol oxidases that may be mentioned include primary alcohols containing from 1 to 6 carbon atoms; donors for the aryl alcohol oxidases that may be mentioned include benzyl alcohol, 4-tert-butylbenzyl alcohol, 3-hydroxy-4-methoxybenzyl alcohol, veratryl alcohol, 4-methoxybenzyl alcohol and cinnamyl alcohol; 2,4-hexadien-1-ol may also be used as donor for the aryl alcohol oxidases.

Generally, the alcohol concentration is between 0.01% and 20% by weight relative to the total weight of the composition, and preferably between 0.05% and 10% by weight relative to the total weight of the composition.

The presence of at least one standard oxidation dye precursor is obligatory when, according to the preferred variant, the dye composition contains an alcohol as substrate.

This standard precursor is optional when the composition according to the invention contains an oxidation dye precursor bearing an alcohol function.

The nature of the standard oxidation dye precursors (bases and/or couplers) used in the composition according to the invention is not critical.

The standard oxidation bases may be chosen especially from para-phenylenediamines, bis(phenyl)alkylenediamines, para-aminophenols, ortho-aminophenols and heterocyclic bases, and the addition salts thereof.

Among the para-phenylenediamines, mention may be made more particularly, by way of example, of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine and 2-β-hydroxyethylamino-5-amino-toluene, and the addition salts thereof with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine and the addition salts thereof with an acid are most particularly preferred.

Among the bis(phenyl)alkylenediamines, mention may be made, by way of example, of N,N'-bis(β-hydroxyethyl)-N,N'-bis (4'-aminophenyl)-1,3-diaminopropanol, N,N'-bis(β-hydroxyethyl) -N,N'-bis(4-aminophenyl)ethylenediamine, N,N'-bis(4-aminophenyl)tetramethylenediamine, N,N'-bis (β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine and 1,8-bis(2,5-diaminophenoxy)-3,6-dioxaoctane, and the addition salts thereof with an acid.

Among the para-aminophenols, mention may be made, by way of example, of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethyl-aminomethyl) phenol and 4-amino-2-fluorophenol, and the addition salts thereof with an acid.

Among the ortho-aminophenols, mention may be made, by way of example, of 2-aminophenol, 2-amino-5-methylphenol, 2-amino-6-methylphenol and 5-acetamido-2-aminophenol, and the addition salts thereof with an acid.

Among the heterocyclic bases, mention may be made, by way of example, of pyridine derivatives, pyrimidine derivatives and pyrazole derivatives.

Among the pyridine derivatives, mention may be made of the compounds described, for example, in patents GB 1 026 978 and GB 1 153 196, such as 2,5-diaminopyridine, 2-(4-methoxyphenyl)amino-3-aminopyridine, and 3,4-diaminopyridine, and the addition salts thereof with an acid.

Among the pyrimidine derivatives, mention may be made of the compounds described, for example, in patents DE 2 359 399; JP 88-169 571; JP 05 163 124; EP 0 770 375 or patent application WO 96/15765, such as 2-hydroxy-4,5,6-triaminopyrimidine, 2,4-dihydroxy-5,6-diaminopyrimidine and pyrazolopyrimidine derivatives such as those mentioned in patent application FR-A-2 750 048, and among which mention may be made of pyrazolo[1,5-a] pyrimidine-3,7-diamine; 2,5-dimethylpyrazolo[1,5-a]-pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo [1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-am-inopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo [1,5-a]pyrimidine-3,7-diamine, 2,5,N7,N7-tetramethylpyrazolo[1,5-a]pyrimidine-3,7-diamine and 3-amino-5-methyl-7-imidazolylpropylamino-pyrazolo[1,5- a]pyrimidine, and the addition salts thereof with an acid, and the tautomeric forms thereof, when a tautomeric equilibrium exists.

Among the pyrazole derivatives, mention may be made of the compounds described in patents DE 3 843 892, DE 4 133 957 and patent applications WO 94/08969, WO 94/08970, FR-A-2,733,749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof with an acid.

Generally, the concentration of this oxidation base is between 0.0005% and 12% by weight relative to the total weight of the composition.

Among standard oxidation couplers that may especially be mentioned are meta-phenylenediamines, meta-aminophenols, meta-diphenols, naphthalenic couplers and heterocyclic couplers, and also the addition salts thereof.

Examples that may be mentioned include 2-methyl-5-aminophenol, 5-N-(β-hydroxyethyl)amino-2-methylphenol, 6-chloro-2-methyl-5-aminophenol, 3-aminophenol, 1,3-dihydroxybenzene (or resorcinol), 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis(β-hydroxyethylamino)toluene, and the addition salts thereof.

Generally, the concentration of this oxidation coupler is between 0.0001% and 10% by weight relative to the total weight of the composition.

In general, the addition salts with an acid that may be used for the oxidation bases and couplers are chosen especially from the hydrochlorides, hydrobromides, sulphates, citrates, succinates, tartrates, lactates, tosylates, benzenesulphonates, phosphates and acetates.

The addition salts that may be used in the context of the invention are chosen, for example, from the addition salts with sodium hydroxide, potassium hydroxide, ammonia, amines and alkanolamines.

According to a second variant of the invention, the substrate for the enzyme is a standard oxidation dye precursor bearing an alcohol function.

In this case, the presence of another standard oxidation dye precursor not bearing an alcohol function is unnecessary. The composition according to the invention may comprise, in a support that is suitable for dyeing, a dye system consisting of at least one oxidation dye precursor bearing at least one alcohol function and at least one alcohol oxidase enzyme.

The said precursor will then be chosen from the oxidation bases below bearing at least one alcohol function, para-phenylenediamines, bis(phenyl)alkylenediamines, para-aminophenols, ortho-aminophenols and heterocyclic bases, and the addition salts thereof, and the oxidation couplers below bearing at least one alcohol function, meta-phenylenediamines, meta-aminophenols, meta-diphenols, naphthalenic couplers and heterocyclic couplers, and also the addition salts thereof.

For the purposes of the present invention, the expression "base or coupler bearing at least one alcohol function" means a compound belonging to one of the families mentioned above, comprising at least one saturated or unsaturated, linear or branched hydrocarbon-based chain containing from 1 to 18 and preferably from 1 to 12 carbon atoms, substituted with at least one OH group and preferably substituted with 1 to 4 OH groups.

Preferably, this precursor will be chosen from the following oxidation bases: N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, N-(β-hydroxypropyl)-para-phenylenediamine, 2-hydroxymethyl-para-phenylenediamine, N-ethyl-N-(β-hydroxyethyl)-para-phenylenediamine, N-(β,γ-dihydroxypropyl)-para-phenylenediamine, 2-β-hydroxyethyloxy-para-phenylenediamine, 2-β-hydroxyethylamino-5-aminotoluene, N,N'-bis(β-hydroxyethyl) -N, N'-bis(4'-aminophenyl)-1,3-diaminopropanol, N,N'-bis(β-hydroxyethyl)-N,N'-bis(4'-aminophenyl)ethylenediamine, N,N'-bis(β-hydroxyethyl)-N,N'-bis(4-aminophenyl)tetramethylenediamine, 4-amino-3-hydroxymethylphenol, 4-amino-2-hydroxymethylphenol, 4-amino-2-(β-hydroxyethylaminomethyl)phenol, 2-(3-aminopyrazolo-[1,5-a]pyrimidin-7-ylamino)ethanol, 2-(7-aminopyrazolo-[1,5-a]pyrimidin-3-ylamino)ethanol, 2-[(3-aminopyrazolo-[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 4,5-diamino-1-(β-hydroxyethyl)pyrazole, 4,5-diamino-1-(β-hydroxyethyl)-3-methylpyrazole, 4,5-diamino-3-hydroxymethyl)-1-methylpyrazole, 4,5-diamino-3-hydroxymethyl-1-isopropylpyrazole, and the following oxidation couplers: 5-N-(β-hydroxyethyl)amino-2-methylphenol, 2,4-diamino-1-(β-hydroxyethyloxy)benzene, 2-amino-4-(β-hydroxyethylamino)-1-methoxybenzene, 1-β-hydroxyethylamino-3,4-methylenedioxybenzene.

When the substrate is an oxidation base bearing an alcohol function, the concentration of this base is between 0.0005% and 12% by weight relative to the total weight of the composition.

When the substrate is an oxidation coupler bearing an alcohol function, the concentration of this coupler is between 0.0001% and 10% by weight relative to the total weight of the composition.

The dye composition in accordance with the invention may also contain one or more direct dyes that may be chosen especially from nitrobenzene dyes, cationic direct dyes and azo, methine and azomethine direct dyes.

The medium that is suitable for dyeing, also known as the dye support, generally consists of water or of a mixture of water and at least one organic solvent to dissolve the compounds that would not be sufficiently water-soluble.

Examples of organic solvents that may be mentioned include $C_1$-$C_4$ lower alcohols, such as ethanol and isopropanol; polyols and polyol ethers, for instance 2-butoxyethanol, propylene glycol, propylene glycol monomethyl ether and diethylene glycol monomethyl ether and monoethyl ether, and also aromatic alcohols, for instance benzyl alcohol or phenoxyethanol, and mixtures thereof.

The solvents may be present in proportions preferably of between 1% and 40% by weight approximately relative to the total weight of the dye composition, and even more preferably between 5% and 30% by weight approximately.

The dye composition in accordance with the invention may also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, mineral or organic thickeners, and in particular anionic, cationic, nonionic and amphoteric polymeric associative thickeners, antioxidants, penetrating agents, sequestering agents, fragrances, buffers, dispersants, conditioners such as, for example, volatile or non-volatile, modified or unmodified silicones, film-forming agents, ceramides, preserving agents and opacifiers.

These above adjuvants are generally present in an amount for each one of between 0.01% and 20% by weight relative to the weight of the composition.

Needless to say, the person skilled in the art will take care to select this or these optional additional compound(s) such that the advantageous properties intrinsically associated with the oxidation dye composition in accordance with the invention are not, or are not substantially, adversely affected by the envisaged addition(s).

The pH of the dye composition in accordance with the invention is generally between 3 and 12 approximately, and preferably between 5 and 11 approximately. It may be adjusted for the desired value using acidifying or basifying agents usually used in the dyeing of keratin fibres, or alternatively using standard buffer systems.

Among the acidifying agents that may be mentioned, for example, are mineral or organic acids, for instance hydrochloric acid, orthophosphoric acid, sulphuric acid, carboxylic acids, for instance acetic acid, tartaric acid, citric acid and lactic acid, and sulphonic acids.

Among the basifying agents that may be mentioned, for example, are aqueous ammonia, alkyl metal carbonates, alkanolamines such as monoethanolamine, diethanolamine and triethanolamine and also derivatives thereof, sodium hydroxide, potassium hydroxide and the compounds of formula (III) below:

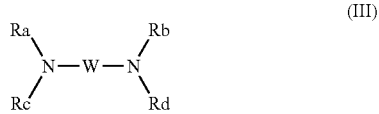

(III)

in which W is a propylene residue optionally substituted with a hydroxyl group or a $C_1$-$C_4$ alkyl radical; Ra, Rb, Rc and Rd, which may be identical or different, represents a hydrogen atom or a $C_1$-$C_4$ alkyl or $C_1$-$C_4$ hydroxyalkyl radical.

The dye composition may be in various forms, such as in the form of liquids, creams or gels, or in any other form that is suitable for dyeing keratin fibres, and especially human hair.

When the oxidation dyes and the alcohol oxidase(s) are present in the same ready-to-use composition, the said composition is preferably free of oxygen gas, so as to avoid any premature oxidation of the oxidation dye(s).

A subject of the invention is also a process for dyeing keratin fibres, and in particular human keratin fibres such as the hair, such that at least one dye composition according to the invention is applied to these fibres, the duration of this application being a period that is sufficient to develop the desired coloration.

The colour is then revealed with atmospheric oxygen or using an oxidizing agent.

The composition is applied to the keratin fibres. After leaving it to act for 3 to 60 minutes approximately and preferably 5 to 40 minutes approximately, the keratin fibres are rinsed, washed with shampoo, rinsed again and then dried.

When the dye composition is a composition in ready-to-use form, it comprises, in a medium that is suitable for dyeing keratin fibres, at least one oxidation dye precursor, at least one alcohol oxidase enzyme and at least one substrate for the said enzyme, and the mixture is then stored in anaerobic form, free of oxygen gas.

According to one variant, this process includes a preliminary step that consists in separately storing, on the one hand, a composition (A) comprising in a medium that is suitable for dyeing keratin fibres, at least one oxidation dye precursor, and, on the other hand, a composition (B) containing, in a medium that is suitable for dyeing keratin fibres, at least one alcohol oxidase enzyme, the composition (A) and/or the composition (B) containing at least one substrate for the said enzyme, and then in mixing together the compositions (A) and (B) at the time of use before applying this mixture to the keratin fibres.

The colour may be revealed at acidic, neutral or alkaline pH and the oxidizing agent may be added to the composition of the invention just at the time of use, or it may be used starting with an oxidizing composition containing it, applied simultaneously or sequentially to the composition of the invention.

The oxidizing composition may also contain various adjuvants conventionally used in compositions for dyeing the hair and as defined above.

The pH of the oxidizing composition containing the oxidizing agent is such that, after mixing with the dye composition, the pH of the resultant composition applied to the keratin fibres preferably ranges between 3 and 12 approximately, and even more preferably between 5 and 11. It may be adjusted to the desired value by means of acidifying or basifying agents usually used in the dyeing of keratin fibres and as defined above.

The composition that is finally applied to the keratin fibres may be in various forms, such as in the form of liquids, creams or gels, or in any other form that is suitable for dyeing keratin fibres, and especially human hair.

Another subject of the invention is a multi-compartment device or dyeing "kit", in which a first compartment contains the composition (A) as defined above and a second compartment contains the composition (B) as defined above. This device may be equipped with a means for applying the desired mixture to the hair, such as the devices described in patent FR-2 586 913 in the name of the Applicant.

The examples that follow serve to illustrate the invention without, however, being limiting in nature.

EXAMPLES

Example 1

The following composition is prepared:

| | |
|---|---|
| para-Phenylenediamine (oxidation base) | 3.2 g |
| Resorcinol (coupler) | 3.3 g |
| Alcohol oxidase from *Pichia pastoris* 5000 U | 2 g |
| Ethanol (donor) | 4 g |
| 0.1 M phosphate buffer in water at pH 9 | qs 100 g |

The above composition is applied to locks of natural grey hair containing 90% white hairs, and left to act for 30 minutes. The hair is then rinsed, washed with a standard shampoo and then dried.

Example 2

| | |
|---|---|
| para-aminophenol (oxidation base) | 3.3 g |
| 2-Methyl-5-aminophenol (coupler) | 3.7 g |
| Alcohol oxidase from *Pichia pastoris* 5000 U | 2 g |
| Ethanol (donor) | 4 g |
| 0.1 M phosphate buffer in water at pH 9 | qs 100 g |

The above composition is applied to locks of natural grey hair containing 90% white hairs, and left to act for 30 minutes. The hair is then rinsed, washed with a standard shampoo and then dried.

Example 3

| | |
|---|---|
| para-Phenylenediamine (oxidation base) | 3.2 g |
| Resorcinol (coupler) | 3.3 g |
| Alcohol oxidase from *Candida boidinii* 2500 U | 2 g |
| Ethanol (donor) | 4 g |
| 0.1 M phosphate buffer in water at pH 9 | qs 100 g |

The above composition is applied to locks of natural grey hair containing 90% white hairs, and left to act for 30 minutes. The hair is then rinsed, washed with a standard shampoo and then dried.

Example 4

| | |
|---|---|
| para-Aminophenol + | 3.2 g |
| para-phenylenediamine (oxidation bases) | 3.3 g |
| Resorcinol (coupler) | 3.3 g |
| Aromatic alcohol oxidase from *Pleurotus pulmonarius* 500 U | 2 g |
| Benzyl alcohol (donor) | 5 g |
| 0.1 M phosphate buffer in water at pH 7 | qs 100 g |

The above composition is applied to locks of natural grey hair containing 90% white hairs, and left to act for 30 minutes. The hair is then rinsed, washed with a standard shampoo and then dried.

Example 5

| | |
|---|---|
| para-phenylenediamine (oxidation base) | 3.2 g |
| 2-Hydroxyethyloxy-ortho-phenylenediamine (coupler and donor) | 5.8 g |
| Aromatic alcohol oxidase from *Pleurotus pulmonarius* 500 U | 2 g |
| 0.1 M phosphate buffer in water at pH 7 | qs 100 g |

The above composition is applied to locks of natural grey hair containing 90% white hairs, and left to act for 30 minutes. The hair is then rinsed, washed with a standard shampoo and then dried.

The hair is dyed in the shades given in the table below:

| EXAMPLE | Shade obtained |
|---|---|
| 1 | Dark chestnut |
| 2 | Coppery |
| 3 | Light chestnut |
| 4 | Chestnut |
| 5 | Violet-blue |

The invention claimed is:

1. Composition for dyeing keratin fibres, and in particular human keratin fibres such as the hair, containing, in a support that is suitable for dyeing, at least one oxidation dye precursor, characterized in that it comprises at least one alcohol oxidase enzyme as sole enzyme for the composition, and at least one substrate for the said enzyme.

2. Composition according to claim 1, such that the alcohol oxidase enzyme belongs to the class E.C.1.1.3 of the enzyme nomenclature.

3. Composition according to claim 2, such that the alcohol oxidase enzyme is chosen especially from primary alcohol oxidases (EC1.1.3.13), secondary alcohol oxidases (EC 1.1.3.18), long-hydrocarbon-chain alcohol oxidases (EC 1.1.3.20), polyvinyl alcohol oxidases (EC 1.1.3.30), vanillyl alcohol oxidase (EC 1.1.3.38) and aromatic alcohol oxidases (EC 1.1.3.7).

4. Composition according to claim 1, such that the alcohol oxidase enzyme is derived from an extract chosen from extracts of plants, of animals or of micro-organisms (bacterium, fungus, yeast, microalga or virus), of differentiated or undifferentiated cells, obtained in vivo or in vitro, unmodified or genetically modified, or synthetic.

5. Composition according to claim 4, such that the alcohol oxidase enzyme is chosen from the genera Pinus, Gastropode, Manduca, Pichia, Candida, Pleurotus and Pseudomonas, and even more particularly from the following species: *Pinus strobus, Gastropode mollusc, Manduca sexta, Pichia pastoris, Candida boidinii, Pleurotus pulmonarius* and *Pseudomonas pseudoalcaligenes.*

6. Composition according to claim 1, such that the concentration of alcohol oxidase enzyme is between 0.005% and 40% by weight relative to the total weight of the said composition.

7. Composition according to claim 1, such that the substrate for the enzyme is an alcohol chosen from primary alcohols, secondary alcohols, long-hydrocarbon-chain alcohols and aromatic alcohols.

8. Composition according to claim 7, such that the alcohol concentration is between 0.01% and 20% by weight relative to the total weight of the composition.

9. Composition according to claim 1, such that it comprises as oxidation dye precursor a standard oxidation base chosen from para-phenylenediamines, bis(phenyl)alkylenediamines, para-aminophenols, ortho-aminophenols and heterocyclic bases, and the addition salts thereof.

10. Composition according to claim 9, such that the concentration of this oxidation base is between 0.0005% and 12% by weight relative to the total weight of the composition.

11. Composition according to claim 1, such that the composition comprises as oxidation dye precursor a standard oxidation coupler chosen from meta-phenylenediamines, meta-aminophenols, meta-diphenols, naphthalenic couplers and heterocyclic couplers, and also the addition salts thereof.

12. Composition according to claim 11, such that the concentration of this coupler is between 0.0001% and 10% by weight relative to the total weight of the composition.

13. Composition according to claim 1, such that the said substrate for the enzyme is an oxidation dye precursor bearing at least one alcohol function.

14. Composition according to claim 13, such that the precursor is chosen from the oxidation bases bearing at least one alcohol function selected from the group consisting of, para-phenylenediamines, bis(phenyl)alkylenediamines, para-aminophenols, ortho-aminophenols and heterocyclic bases, and the addition salts thereof, and the oxidation couplers bearing at least one alcohol function selected from the group consisting of, meta-phenylenediamines, meta-aminophenols, meta-diphenols, naphthalenic couplers and heterocyclic couplers, and also the addition salts thereof.

15. Composition according to claim 14, such that the precursor is chosen from the following oxidation bases: N,N-bis($\beta$-hydroxyethyl)-para-phenylenediamine, 4-N,N-bis($\beta$-hydroxyethyl)amino-2-methylaniline, 4-N,N-bis(J3-hydroxyethyl)amino-2-chloroaniline, 2-$\beta$-hydroxyethyl-para-phenylenediamine, N-($\beta$-hydroxypropyl)-para-phenylenediamine, 2-hydroxymethyl-para-phenylenediamine, N-ethyl-N-($\beta$hydroxyethyl)-para-phenylenediamine, N-($\beta$,$\gamma$-dihydroxypropyl)-para-phenylenediamine, 2-$\beta$-hydroxyethyloxy-para-phenylenediamine, 2-$\beta$-hydroxy-ethylamino-5-aminotoluene, N,N'-bis($\beta$-hydroxyethyl)-N,N'-bis(4'-aminophenyl)-1,3-di-aminopropanol, N,N'-bis($\beta$-hydroxyethyl)-N,N'-bis(4'-aminophenyl)ethylenediamine, N,N'-bis($\beta$-hydroxyethyl)-N,N'-bis(4-aminophenyl)tetramethylenediamine, 4-amino-3-hydroxymethylphenol, 4-amino-2-hydroxymethylphenol, 4-amino-2-($\beta$-hydroxyethylaminomethyl)phenol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-amino-pyrazolo [1,5-a]pyrimidin-3-yl)(2-hydroxyethyl)amino]ethanol, 4,5-diamino-1-($\beta$-hydroxy-ethyl)pyrazole, 4,5-diamino-1-($\beta$-hydroxyethyl)-3-methylpyrazole, 4,5-diamino-3-hydroxymethyl)-1-methylprazole, 4,5-diamino-3-hydroxymethyl-1-isopropylpyrazole, and the following oxidation couplers: 5-N-($\beta$-hydroxyethyl)amino-2-methylphenol, 2,4-di-amino-1-($\beta$-hydroxyethyloxy)benzene, 2-amino-4-($\beta$-hydroxyethylamino)-1-methoxybenzene, 1-$\beta$-hydroxyethylamino-3,4-methylenedioxybenzene.

16. Composition according to claim 1, characterized in that it contains one or more direct dyes.

17. Composition according to any one of claims 9, 11 and 14, such that the addition salts are chosen from the hydrochlorides, hydrobromides, sulphates, citrates, succinates, tartrates, lactates, tosylates, benzenesulphonates, phosphates, acetates and the addition salts with sodium hydroxide, potassium hydroxide, ammonia, amines or alkanolamines.

18. Dye composition for keratin fibres, containing, in a support that is suitable for dyeing, a dye system consisting of at least one oxidation dye precursor bearing at least one alcohol function and at least one alcohol oxidase enzyme.

19. Dye composition according to claim 18, characterized in that the alcohol oxidase enzyme belongs to the class E.C.1.1.3 of the enzyme nomenclature.

20. Ready-to-use composition, containing, in a support that is suitable for dyeing, at least one oxidation dye precursor, at least one alcohol oxidase enzyme as sole enzyme and at least one substrate for the said enzyme, the mixture being stored in anaerobic form, free of oxygen gas.

21. Process for dyeing keratin fibres, and in particular human keratin fibres such as the hair, characterized in that at least one composition according to claim 1 is applied to the said fibres, for a period that is sufficient to develop the desired coloration.

22. Process according to claim 21, characterized in that it includes a preliminary step that consists in separately storing, on the one hand, a composition (A) comprising in a medium that is suitable for dyeing keratin fibres, at least one oxidation dye precursor, and, on the other hand, a composition (B) containing, in a medium that is suitable for dyeing keratin fibres, at least one alcohol oxidase enzyme, the composition (A) and/or the composition (B) containing at least one substrate for the said enzyme, and then in mixing together the compositions (A) and (B) at the time of use before applying this mixture to the keratin fibres.

23. Process for dyeing keratin fibres, characterized in that at least one composition according to claim 18 is applied to the said fibres, for a period that is sufficient to develop the desired coloration.

24. Process for dyeing keratin fibres, and in particular human keratin fibres such as the hair, characterized in that the composition according to claim 20 is applied to the said fibres, for a period that is sufficient to develop the desired coloration.

25. Multi-compartment device or dyeing kit, characterized in that it comprises a first compartment containing acomposition (A) and a second compartment containing a composition (B), said composition (A) comprising in a medium that is suitable for dyeing keratin fibres, at least one oxidation dye precursor, and, said composition (B) containing, in a medium that is suitable for dyeing keratin fibres, at least one alcohol oxidase enzyme, as sole enzyme, the composition (A) and/or the composition (B) containing at least one substrate for the said enzyme.

26. Multi-compartment device or dyeing kit, characterized in that it comprises a first compartment containing the composition (A) comprising in a medium that is suitable for dyeing keratin fibres, at least one oxidation dye precursor, and, a second compartment containing the composition (B) containing, in a medium that is suitable for dyeing keratin fibres, at least one alcohol oxidase enzyme, as sole enzyme, the composition (A) and/or the composition (B) containing at least one substrate for the said enzyme, the whole device being stored in anaerobic form, free of oxygen gas.

27. Multi-compartment device or dyeing kit, characterized in that it comprises a first compartment containing the composition (A) comprising in a medium that is suitable for dyeing keratin fibres, at least one oxidation dye precursor bearing at least one alcohol function, and, a second compartment containing the composition (B) containing, in a medium that is suitable for dyeing keratin fibres, at least one alcohol oxidase enzyme, as sole enzyme.

28. Composition according to claim 1, such that the concentration of alcohol oxidase enzyme is between 0.05% and 10% by weight relative to the total weight of the said composition.

29. Composition according to claim 7, such that the alcohol concentration is between 0.05% and 10% by weight relative to the total weight of the composition.

* * * * *